US011980695B2

(12) United States Patent
Silverman

(10) Patent No.: US 11,980,695 B2
(45) Date of Patent: May 14, 2024

(54) PROCESS AND SYSTEM FOR ULTRASONIC DRY MIST DISPENSER AND OZONE SANITIZER

(71) Applicant: David Silverman, Indian Harbour Beach, FL (US)

(72) Inventor: David Silverman, Indian Harbour Beach, FL (US)

(73) Assignee: David Silverman, Indian Harbour Beach, FL (US)

(*) Notice: Subject to any disclaimer, the term of this patent is extended or adjusted under 35 U.S.C. 154(b) by 338 days.

(21) Appl. No.: 17/320,957

(22) Filed: May 14, 2021

(65) Prior Publication Data

US 2021/0353802 A1 Nov. 18, 2021

Related U.S. Application Data

(60) Provisional application No. 63/025,649, filed on May 15, 2020.

(51) Int. Cl.
*A61L 2/20* (2006.01)

(52) U.S. Cl.
CPC ......... *A61L 2/202* (2013.01); *A61L 2202/121* (2013.01); *A61L 2202/122* (2013.01); *A61L 2202/14* (2013.01); *A61L 2202/20* (2013.01)

(58) Field of Classification Search
CPC ........ A61L 2/202; A61L 2/26; A61L 2202/15; A61L 2209/212; A61L 2/22
See application file for complete search history.

(56) References Cited

U.S. PATENT DOCUMENTS 4,035,301 A 7/1977 Armstrong
6,726,166 B2 4/2004 Gaaloul et al.
(Continued)

FOREIGN PATENT DOCUMENTS

DE 20007336 U 4/2010
DE 102017210854 A 1/2019
(Continued)

OTHER PUBLICATIONS

International Search Report in related application PCT/US2021/032624 dated Sep. 15, 2021; 4 pages.
(Continued)

*Primary Examiner* — Sean E Conley
*Assistant Examiner* — Justin Hwang
(74) *Attorney, Agent, or Firm* — Mark Malek; Widerman Malek, PL

(57) ABSTRACT

The system of the present invention is for treating surfaces and airborne particles comprising. The system includes an exterior housing and an enclosed water storage tank mounted inside the exterior housing to store water. The system may also include a dry mist generator mounted on a water float to position the dry mist generator below a surface of the water stored in the enclosed water storage tank. The system may further include an air blower having an outlet connected to water storage tank above a predetermined water level. The system may still further include an oxygen tank having an outlet, and an ozone generator connected to the outlet of the oxygen tank. The system may also include a regulator and flow meter connected to the outlet of the oxygen tank and having an inlet conduit to the ozone generator to regulate a flow of oxygen into the ozone generator.

17 Claims, 5 Drawing Sheets

(56) References Cited

U.S. PATENT DOCUMENTS

Figure 1A:
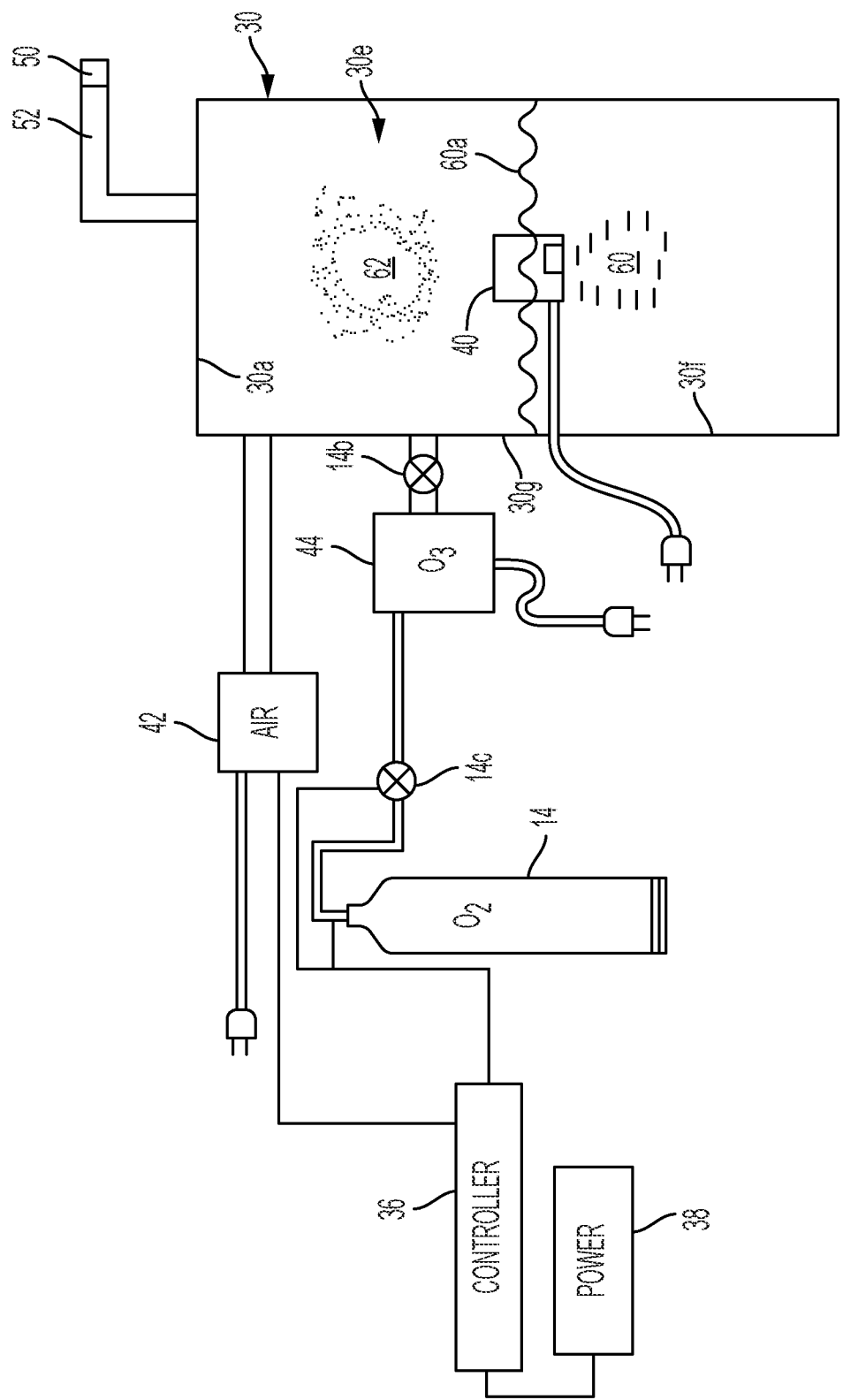

| | | | |
|---|---|---|---|
| 7,604,774 B2* | 10/2009 | Mole | A61L 9/015 |
| | | | 422/123 |
| 8,414,839 B1 | 4/2013 | Barnes | |
| 2002/0185423 A1 | 12/2002 | Boyd et al. | |
| 2008/0226495 A1* | 9/2008 | Sparks | A61L 2/22 |
| | | | 422/128 |
| 2018/0327264 A1* | 11/2018 | Sato | C01B 13/11 |
| 2019/0038794 A1 | 2/2019 | Reddy et al. | |

FOREIGN PATENT DOCUMENTS

| | | |
|---|---|---|
| EP | 3108974 A1 | 12/2016 |
| WO | 2007012226 A1 | 2/2007 |
| WO | 2008069774 A2 | 6/2008 |
| WO | WO-2008069774 A2 * 6/2008 ............. A61L 2/202 |

OTHER PUBLICATIONS

Written Opinion in related application PCT/US2021/032624 dated Sep. 15, 2021; 8 pages.

\* cited by examiner

PROCESS AND SYSTEM FOR ULTRASONIC DRY MIST DISPENSER AND OZONE SANITIZER

RELATED APPLICATIONS

This application claims priority under 35 U.S.C. § 119(e) of U.S. Provisional Patent Application Ser. No. 63/025,649 filed on May 15, 2020 and titled ULTRASONIC DRY MIST DISPENSER AND OZONE SANITIZER. The content of this application is incorporated herein by reference.

FIELD OF THE INVENTION

This invention relates generally to sanitization, sterilization, and disinfection of surfaces and, more specifically, to a process and system for generating a dry mist saturated with dissolved ozone and dispensing the dry mist saturated with dissolved ozone on surfaces for sanitization purposes. Further, the invention relates to sanitization, sterilization, and disinfection of hard and soft surfaces, as well as airborne particles, including, but not limited to, free bacteria and/or viruses.

BACKGROUND OF THE INVENTION

The recent worldwide pandemic of the COVID-19 virus has created an urgent demand for a sanitization and/or disinfection process and system that can disinfect and sanitize hard and soft surface and airborne particles in a fast and efficient manner to remove bacteria and viruses.

Numerous processes and systems using liquid disinfectants that are typically sprayed onto surface areas and into ambient air are well known in the art. Prior art systems, however, may have deleterious effects on an individual as liquid disinfectants can leave toxic chemicals on a surface or create toxic vapors in the surrounding air. Thus a liquid disinfectant may affect an exposed person causing various health disorders.

Some ozone generating machines rely on introducing ozone gas into ambient air. This is inadequate for quick and safe dispersion of ozone molecules for sanitization, disinfection, and health issues. Because ambient air ozone gas generating machines utilize ambient air to produce ozone, and the air can contain copious amounts of Nitrogen and humidity, it results in air surfaces that can include Nitric Oxides and Nitric acid.

In light of the above deficiencies in the prior art, a solution is needed that provides a system and process to treat, disinfect, sanitize, and sterilize hard and soft surfaces, as well as airborne particles, and that avoids introduction of harmful chemicals.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

The present invention addresses the deficiencies in the prior art by providing a process and system that produces a fine dry mist that is slightly super-saturated with ozone sanitizer and/or disinfectant that can be quickly and efficiently distributed and dispensed onto surfaces and airborne particles producing a high sanitization and/or disinfection rate of viruses and bacteria.

The process according to embodiments of the present invention includes the steps of ultrasonically generating a dry water mist saturated with ozone, and dispensing the dry mist saturated with ozone onto hard and soft surfaces and airborne particles for disinfecting the hard and soft surfaces to remove bacteria and viruses. The present invention advantageously generates and dispenses the dry mist saturated with ozone without leaving a wet surface. The improved system according to the present invention includes a piezo electrically ultrasonically generated, substantially dry mist saturated or slightly supersaturated ozone mist dispensing and sanitizing and/or disinfecting system for hard and soft surfaces and airborne particles. In some embodiments of the present invention, 80-90 and up to 150 parts per million of dissolved ozone in the dry mist are produced. In some embodiments, the system may comprise an exterior housing, a water storage tank mounted inside the exterior housing, An Oxygen ($O_2$) supply tank attached to the outside of the exterior housing, and an air blower connected on a side wall of the internal water storage tank. The air blower may have an air flow outlet opening into the water storage tank. The air flow outlet opening may be positioned above the surface of a predetermined water level of water stored in the water tank. In some embodiments, the predetermined water level may be defined as a predetermined maximum water level. The air flow outlet of the air blower in the water storage tank may include an input air flow diverter which may be configured to direct incoming air in a direction toward the water surface.

An ozone generator conduit outlet may be mounted and configured to open into the water storage tank. More specifically the ozone generator conduit outlet is preferably positioned on a vertical wall of the water storage tank that includes the air blower outlet and above the water storage tank maximum water surface level, but below the air blower outlet into the water storage tank, so that incoming ozone is directed just above the water surface.

A dry mist generating device may also be provided to generate a fine dry mist. In some embodiments, the dry mist generating device may, for example, be provided by a piezoelectric ultrasonic oscillator. The dry mist generating device may be positioned inside the water storage tank. More particularly, the dry mist generating device is preferably positioned on a water float, just below the water surface. Its structure and function are described below.

An elongate flexible saturated dry mist ozone dispensing hose, used for ozone sanitizing hard and soft surfaces and airborne particles, may be connected by an access fitting hose fastener to an access fitting. The access fitting hose fastener may, for example, be provided by a threaded or quick disconnect opening in the exterior housing top flat surface. The elongate flexible saturated dry mist ozone dispensing hose may also be connected internally to the top to an access fitting opening in the top surface of the internal water storage tank. The dispensing hose may emit the ozone saturated dry mist from the upper volume of the water storage tank, above the water surface, dispensing the ozone saturated dry mist produced in the water storage tank through the dispensing hose onto hard and soft surfaces and airborne particles for disinfecting and sanitizing, without leaving a moist residue on the surfaces.

The top surface of the exterior housing and the top surface of the water storage tank may both include second access fittings with openings. Each fitting may be connected to a second conduit to receive inlet water that allows the water storage tank to be filled with water from outside of the water storage tank and from outside of the exterior housing. The inlet water conduit can include a removable threaded cap at the exterior housing access fitting opening which is also threaded.

The water storage tank may, in some embodiments, be a cube or rectangular prism, with six sides, each rectangular in shape, with four vertical side surfaces, a flat bottom surface, and a substantially top flat surface. Those skilled in the art, however, will appreciate that the water storage tank may also have a cylindrical shape. The volume of the water in the water storage tank, during operation, may be determined by a predetermined maximum water level, the height or depth of the water in the water storage tank vertically. One or more water level sensor lights may be provided on the exterior housing door to show the maximum fill level. The water level sensor lights may, for example, be illuminated when a desired amount of water is positioned in the tank, and/or when a minimum acceptable level of water is achieved in the water storage tank. The water storage tank may have a specifically predetermined upper vertical side wall water level position. It is preferably that the water storage tank not be filled above the certain designated level vertically in the water storage tank. The water storage tank may also have a minimal water level for operation, unless one desires to empty the water storage tank, for which there is a drain valve provided at the very bottom of the water tank.

The process of generating a fine water mist and saturating the fine water mist with ozone to create an ozone saturated dry mist with a predetermined desired amount of ozone in parts per million, which, when dispensed onto a hard or soft surface, and/or airborne particles, may provide treatment, disinfection, sanitation and/or sterilization thereof without getting a surface wet. The water storage tank water maximum level position may be manipulated to enhance operation of the present invention.

In order to create a desired ratio of ozone ($O_3$) to saturate the ozone saturated dry mist generated by the dry mist generating device, which may be submerged just below the water level surface, e.g., ½ inch in some embodiments, the air blower outlet air flow, with a downward air diverter, may be positioned above the water storage tank water level. This advantageously allows incoming air to be directed downwardly toward the water surface in the water storage tank. More specifically, the incoming air may be directed through an air blower outlet opening above the water surface. The air blower outlet opening may extend from the water storage tank side wall exterior mounted air blower on the inside of the water storage tank. The air blower outlet opening may provide an air flow directing surface outlet that forces the air downwardly from the air blower outlet and toward the water surface level. The ozone generator outlet may, in some embodiments of the present invention also be mounted on the water storage tank sidewall. More particularly, in some embodiments, the ozone generator outlet may be positioned closer to the inside water surface level position so that the incoming flowing ozone will be distributed to flow just above the water surface level. This positioning of the ozone outlet producing the ozone saturated dry mist in the water storage tank, along with the air blower dispersing air downwardly towards the water, advantageously creates a desirable ratio and mixture of dry mist and ozone to saturate, or slightly supersaturate, the dry mist with ozone for enhanced sanitization and/or disinfection of surfaces and airborne particles. In some embodiments, 80-90 and up to 150 parts per million of ozone in the ozone saturated dry mist is desirable for treatment, sanitization, disinfection, and/or sterilization.

In some embodiments, an ultrasonic oscillator in the form of piezoelectric ceramic discs may produce the dry mist to be ozone saturated in the water storage tank. The ultrasonic oscillator may be positioned in a cylindrical, doughnut-shaped floating unit with a central, circular support surface area. The floating unit may be a substantially flat planar support surface containing a plurality of the ultrasonic oscillator discs. The ultrasonic oscillator discs may be arranged in a substantially horizontally parallel configuration. In some embodiments, as many as 12 ceramic ultrasonic oscillator discs may be provided, but those skilled in the art will appreciate that any number of ultrasonic oscillator discs may be provided while still carrying out the objects, features, and advantages of the present invention. The planar support surface and ultrasonic oscillator discs (supported in the center of the floating doughnut-shaped unit) may be located just below the surface of the water, and preferably at least one-half inch below the surface of the water. Each ceramic disc is preferably positioned at substantially the same level, but those skilled in the art will appreciate that the ceramic discs may also be positioned at different levels while still carrying out the objects, features and advantages of the present invention. Each of the ultrasonic oscillator discs may be electrically connected to a power source so that all of the ultrasonic oscillator ceramic discs are in electrical communication and may be configured to operate simultaneously. The ultrasonic frequency generated thereby converts the water into a dry mist of droplets into the upper portion of a water storage tank blending chamber, above the water level, filling the blending chamber with dry mist that is saturated with ozone. The droplets are preferably micron and/or sub-micron sized droplets.

The ozone ($O_3$) generator outlet, mounted to the water storage tank vertical wall, may have an inlet conduit with operating pressure valves in communication with the oxygen tank in order to receive oxygen ($O_2$) from the oxygen storage tank. The separate oxygen supply ($O_2$) tank is preferably mounted on the exterior wall or door of the exterior housing. The oxygen supply tank provides oxygen to the ozone generator, which advantageously allows for the dry mist particles to be saturated with ozone without creating hazardous components. The oxygen tank outlet conduit can include oxygen flow and pressure regulating valves. The ozone generator output flow may be injected into the water storage tank, above the water surface, in conjunction with the air blower outlet air flow into the water storage tank. The volume above the water level in the water storage tank, which may be defined as the blending chamber, may be filled with dry mist to be saturated with ozone. The operation of the air blower aids in dispensing the dry mist becoming saturated with ozone for sanitizing and/or disinfecting into the dispensing hose and onto hard and soft surfaces and airborne particles. The dry mist saturated with ozone is collated into a thoroughly mixed, fine particle, sanitizing and/or disinfecting mixture that may become super-saturated with ozone, in some embodiments, 80-90 and up to 150 parts per million of ozone.

The ozone saturated dry mist, once formed, may be power dispersed, under low pressure, from a dispenser hose outlet that dispenses the ozone saturated dry mist onto surrounding solid and porous surfaces, as well as airborne particles, for sanitizing and/or disinfecting. The saturated dry mist, however, does not deposit a wet residue on surfaces when dispensed thereon for sanitization and disinfection purposed.

The process according to the present invention may, in some embodiments, be provided from a mobile platform. The mobile platform may have four wheels and a manual pushing handle that includes the dry mist, oxygen supply, and ozone mixing components described herein, including the delivery system, so that the portable system can be easily moved from one area to another area for use.

Accordingly, it is an object of the invention to provide a process and system for generating an ozone saturating dry mist using an ultrasonic oscillator, saturating the dry mist with a predetermined amount of ozone per million parts for the mixture, and dispensing the mixture of ozone saturated dry mist onto hard and soft surfaces, as well as airborne particles, into the ambient air for sanitizing and/or disinfecting surfaces of viruses and bacteria, without wetting the surfaces.

BRIEF DESCRIPTION OF THE DRAWINGS

Some embodiments of the present invention are illustrated as an example and are not limited by the figures of the accompanying drawings, in which like references may indicate similar elements.

FIG. 1A shows a schematic, perspective view of the process and system piezoelectric ultrasonic oscillator used in the invention, inside the water storage tank FIG. 1B is a perspective view of the exterior housing of a portable embodiment of the invention showing a portable ultrasonic oscillator ozone saturated dry mist dispenser and ozone sanitizer exterior housing.

FIG. 2 is a perspective view of the portable embodiment shown in FIG. 1B within an end door open, showing an internal water storage tank inside said portable embodiment exterior housing.

FIG. 3 shows an exploded, perspective view of the portable embodiment shown in FIG. 1 and FIG. 2, with the water storage tank exploded upwardly from the exterior housing and also showing the internal water storage tank exploded to illustrate an ultrasonic oscillator ozone saturated dry mist generator that is utilized inside the water storage tank.

FIG. 4 shows a side elevational view of the portable embodiment of the invention disclosed in FIGS. 1B-3, partially cutaway, exposing a portion of the water storage tank shown in elevation and in cross-section.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as “above,” “below,” “upper,” “lower,” and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as “generally,” “substantially,” “mostly,” and other terms are used, in general, to mean that the referred to object, characteristic, or quality constitutes a majority of the subject of the reference. The meaning of any of these terms is dependent upon the context within which it is used, and the meaning may be expressly modified.

FIG. 1A shows a schematic diagram to of the crux of the invention, which is a process and system to generate an ozone saturated dry mist in an enclosed water storage tank 30 using an ultrasonic oscillator 40, generate ozone from oxygen and mix the ozone with the dry mist to saturate with dissolved ozone, and dispense the ozone saturated dry mist through a dispensing hose 52 onto hard surfaces, soft surfaces and to be in fluid communication with airborne particles to sanitize, sterilize, and/or disinfect and or deactivate bacteria and viruses. The provision of a dry mist by the present invention advantageously allows for the above features to be carried out without surface wetting.

To generate dry mist, air from air blower 42 (under low pressure) and ozone from ozone generator 44 are preferably simultaneously directed into the blending chamber 30*e* in water storage tank 30 above the surface 60*a* of the water 60. The present invention also includes a dry mist generator. The dry mist generator may, for example, be provided by an ultrasonic oscillator 40 that generates dry mist that rises into air flow and ozone flow volume ratios to saturate the dry mist blending chamber area 30*e* completely with and ozone saturated dry mist. Those skilled in the art will appreciate that the dry mist generator may also be provided by other devices, and the use of other devices to provide dry mist is contemplated to be included in the present invention. The ozone saturated dry mist in chamber 30*e* is directed, under low relative pressure, through a distribution and sanitizer hose 52 and out a nozzle 50 onto a desired hard or soft surface and airborne particles to be sanitized and/or disinfected, without wetting the surface.

An electronic controller 36 may be used to operate and manage distribution of the ozone saturated dry mist, and to control the generation of ozone from the oxygen supply tank 14 supply and pressure valves 14*b*, 14*c*, and to ensure and maintain saturation quantity and ratios for the sanitation and/or disinfecting ozone saturated dry mist for maximum efficiency. The overall air blower air and oxygen used in the ozone generator, as well as ozone flow rates, control the amount of ozone to saturate into the dry mist in the water storage tank blending chamber 30*e* to obtain an optimum ratio of dry mist and ozone for sanitizing and/or disinfecting hard and soft surfaces and airborne particles, and generation control ratios is the responsibility of sensors and the controller 36 in its operation of all of the essential components of the system.

Referring now to FIG. 1B, the ultrasonic ozone saturated dry mist dispenser and ozone sanitizer and/or disinfection system exterior housing 12 described herein is shown, in one embodiment, as a portable system 10, that includes an exterior housing 12 having three rectangular, vertical sides 12e, a rectangular door 12c that opens outwardly, a bottom panel, top rectangular panel 12a that includes two threaded access fitting ports 12b and 12d, with caps. One of the access fitting ports 12b is used to allow water to be poured into the water storage tank inside the exterior housing 12. The other access fitting 12d is used to connect to a system ozone saturated dry mist sanitizer dispensing hose (not shown) in FIG. 1B.

Those skilled in the art will appreciate that although the exterior housing 12 is shown as having three rectangular, vertical sides, the housing may be provided in any shape, and the door may also be provided to have any shape. Further, although the door is depicted as opening outwardly, it is contemplated that the door may also open inwardly.

The mobile platform exterior housing 12 may include manual handle 18 and four wheels 16 that allow the system 10 to be manually positioned and moved to different desired locations for sanitizing and disinfecting with a dispensing hose and nozzle, in some embodiments.

Door 12c supports an oxygen tank 14 that is secured to the door 12c by a support bracket 20 that firmly holds the oxygen tank 14 in place, while being suspended and attached to housing 12. An oxygen tank 14 manual on/off flow valve 14a is provided on oxygen tank 14. Another on/off flow valve 22 and oxygen pressure gauges 24 that can measure the pressure in the oxygen tank 14, while on/off flow valve 22 allows the oxygen tank to be turned on and off when providing oxygen to an ozone generator 44, (FIG. 2), discussed below. Also mounted on door 12c is a system on-off power switch 26, and four status lights 28 that provide status of the system 10 operation, power on and off, the sanitizing operation is "on," high water level, and minimum water level in the water storage tank. Another status light could show low oxygen O2. Those skilled in the art will appreciate that although four status lights are shown, the objects, features and advantages of the present invention may be provided and carried out using any number of status lights to indicate any number of notifications to a user.

Figure 2:
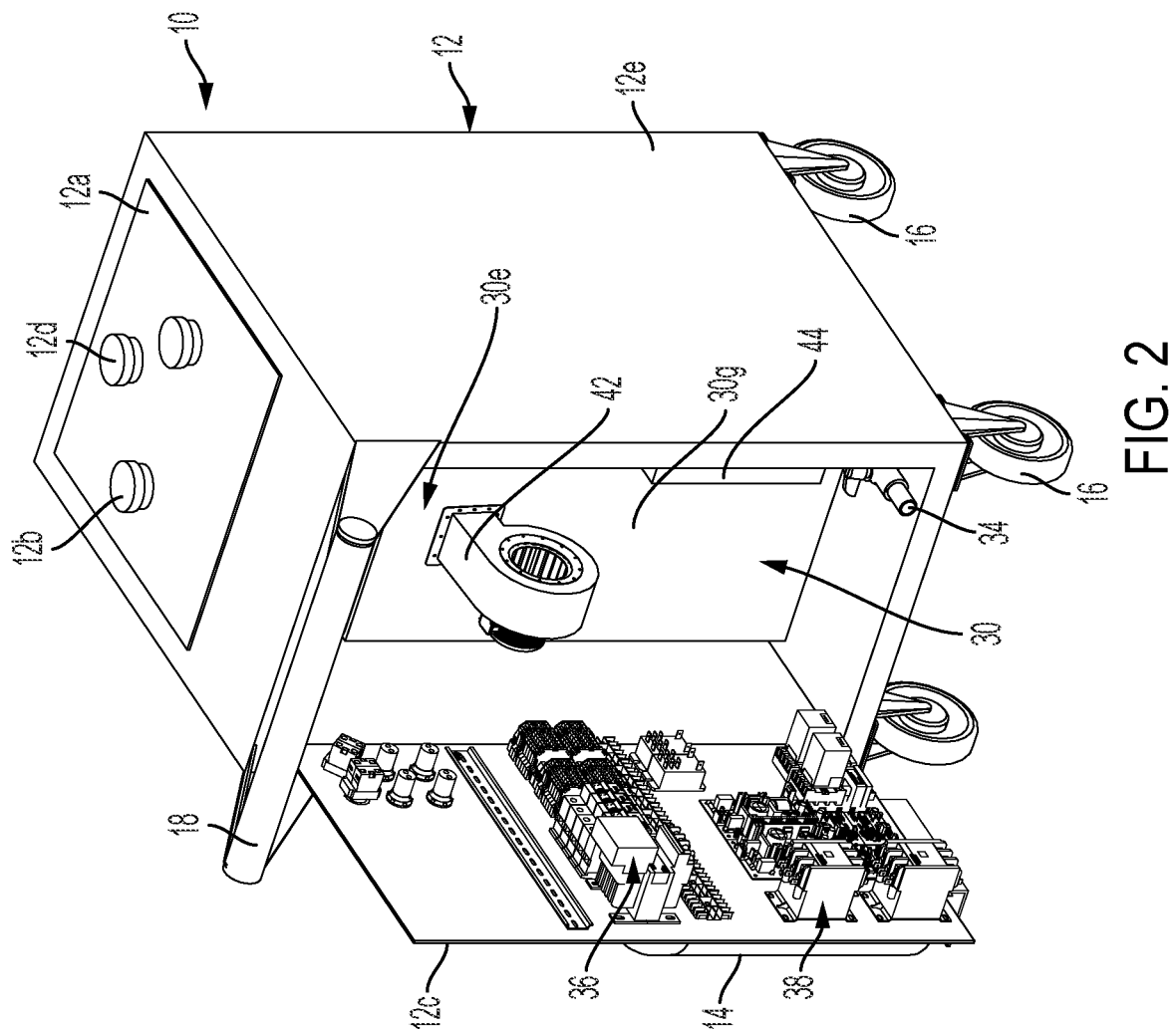

Referring now to FIG. 2, the system 10 is shown, with door 12c in the open position. The inside of the exterior housing 12, and the components and equipment that generate the ozone saturated dry mist and dispense the ozone saturated dry mist for sanitation, sterilization, deactivation and/or disinfection are shown.

A major component of the system 10 is a water storage tank 30 that occupies a volume inside of the exterior housing 12. The water storage tank 30 is substantially a rectangular six-sided cube or rectangular prism that is used to receive and store pure water. Although a rectangular shape for the exterior housing 12 is shown, those skilled in the art will appreciate that the shape of the housing can be anything while still carrying out the objects, features and advantages according to the present invention. The water, vibrated by an ultrasonic oscillator, becomes the ozone saturated dry mist used in the invention. The water storage tank 30 has rigid metal walls that are substantially rectangular, a rectangular floor or base and a rectangular top that has at least two access fittings around ports. Although a rectangular shape of the water storage tank is described above, those skilled in the art will appreciate that the water storage tank may have any shape while still carrying out the advantages, features, and benefits according to the present invention. For example, the water storage tank may be cylindrical in shape. Further, those skilled in the art will appreciate that the present invention may include a plurality of water storage tanks. One access fitting port is for receiving water to be used in the water storage tank and a second access fitting port is for dispensing the ozone saturated dry mist sanitizer from the water storage tank 30, described in detail below. It is preferable that the water used in the water storage tank is purified water, or filtered water, but those skilled in the art will appreciate that any other type of water can also be used, such as, for example, distilled water.

In FIG. 2, an air blower 42 and its outlet are attached to one of the vertical water storage tank 30 side walls 30g. An ozone generator 44 is attached physically to the inside of exterior vertical wall 12e and has an outlet conduit (not shown) attached to the same vertical water storage tank wall 30g as the air blower 42. Thus, air that is blown into the water storage tank 30 from the same vertical side wall 30g as ozone is being directed into the water storage tank 30 from the same side wall 30g is shown below. The water storage tank 30 may have sensors (not shown in FIG. 2) to determine the maximum and minimum water levels permitted in the water storage tank so that the incoming air from air blower 32 along with the incoming ozone directed into the water storage tank 30 are above the water surface.

Inside the water storage tank 30 there is an inductive outside float, housing an ultrasonic oscillator used to generate the dry mist that gets mixed by incoming air from air blower 42 along with ozone being generated by ozone generator 44. This operation is discussed below. Near the bottom of the water storage tank 30 is a drain and drain valve 34 that allows the water storage tank 30 to be drained by gravity when necessary to remove any undesired water. FIG. 2 shows, mounted on door 12c on the inside, an electrical control unit 36 and an electrical power unit 38, all of which may include the logic circuits and power necessary for controlling the air blower 42, the ozone generator 44 for generating ozone and operating the dry mist ultrasonic oscillator (that floats inside the water storage tank 30). Electronic operating units 36 and power units 38 also control solenoid valves and the flow rates of the air coming from blower 42 and the dispensing rate of dry mist to achieve the proper proportions of dry mist and ozone to create the ozone saturated dry mist for use in the system 10, discussed below.

Figure 1B:
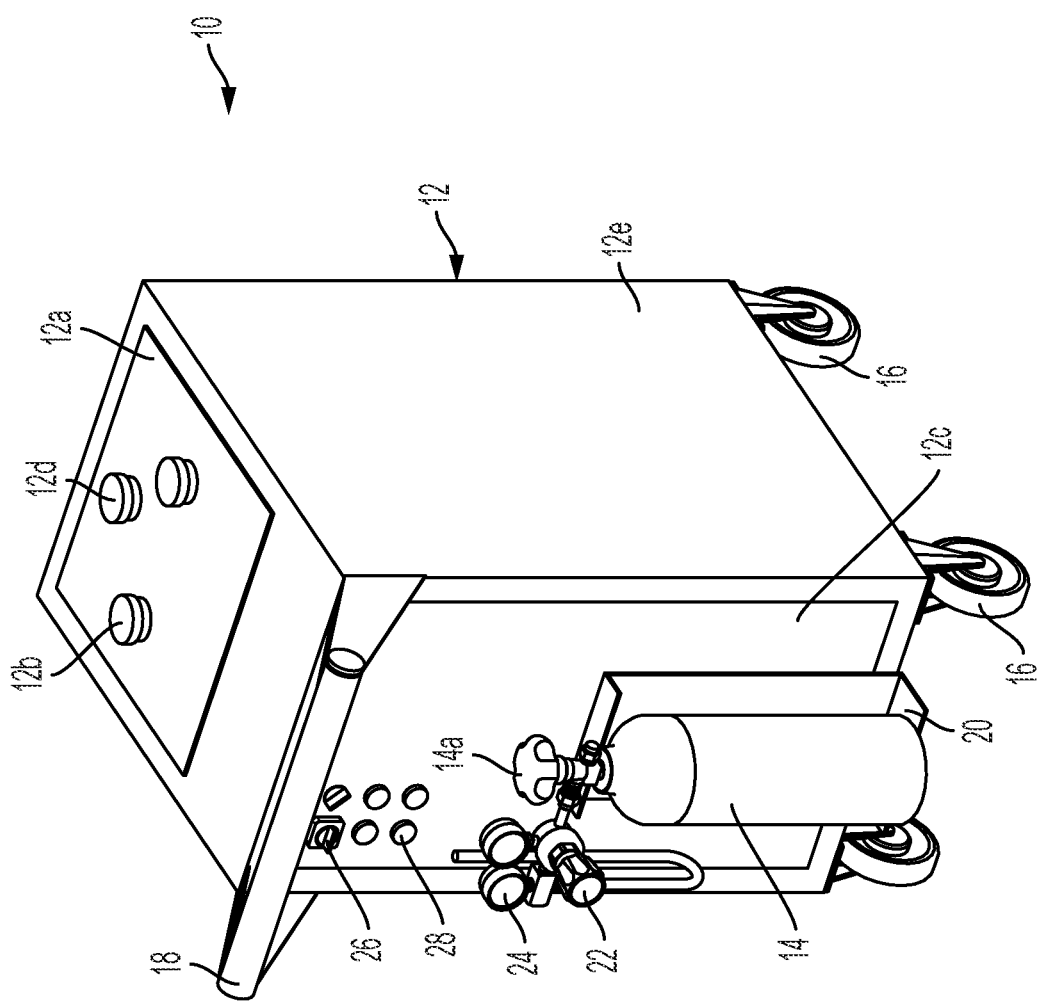
Figure 3:
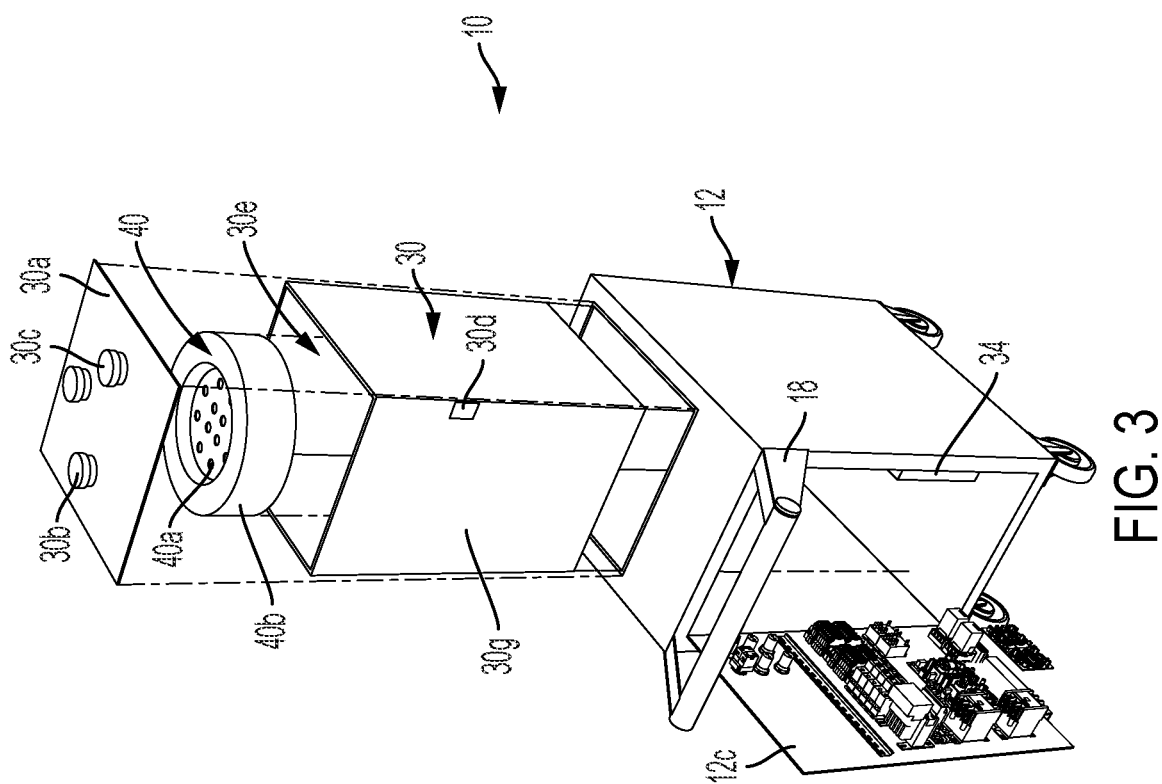

Referring now to FIG. 3, an exploded view of system 10 is shown. The water storage tank 30 is shown elevated, for illustration purposes, above the exterior housing 12. The water storage tank 30 includes an enclosed, six-sided rectangular prism that includes a rigid metal top surface 30a that has two access fittings and ports 30b and 30c. Those skilled in the art will appreciate that although the water storage tank 30 is depicted as a six-sided rectangular prism, it can be provided by any shape such as, for example, a cylindrical storage tank. Access fitting 30b is a port to receive pure water that is deposited into the water storage tank 30 when necessary. Access fitting 30c is a port used to dispense the ozone saturated dry mist sanitizer and/o disinfectant, generated in the water storage tank 30 mixing chamber 30e. Each access fitting port, 30b and 30c, is connected to the lid (not shown in FIG. 3) to a comparably functioning access fitting port, directly above, in exterior housing 12a top panel, shown as access fittings ports 12b and 12d (FIG. 1). The exterior housing access fitting port 12b can be connected by a conduit to the water storage tank 30 to allow the input of water from outside the exterior housing 12 into the water storage tank 30 in order to fill the water storage tank to the correct level with water. Access fitting port 12d, FIG. 1, in the exterior housing panel 12a, is connected to a conduit (not shown in FIG. 3) attached to water storage tank top panel access fitting port 30*c* disposed in the top panel 12*a* of the exterior housing, that connects to a dispensing hose (FIG. 1A) for dispensing the ozone saturated dry mist ozone sanitizer from inside water storage tank 30 blending chamber 30*e*.

In FIG. 3, the water storage tank 30 contains inside an ultrasonic oscillator 40 (elevated above for illustration purposes). The ultrasonic oscillator 40 is an ultrasonic transducer that generates ultrasonic frequencies from a piezoelectric crystal using ceramic discs submerged in water in the water storage tank to generate dry mist in the water storage tank blending chamber, 30*e* above the water surface. The water storage tank 30 includes a water level sensing device 30*d* that sets the displays maximum height (or depth) of water in the water storage tank 30. The ultrasonic oscillator 40 includes a float 40*b*, that is doughnut-shaped in some embodiments. The float 40*b* may be connected to an interior flat panel that includes a plurality of ultrasonic oscillator (frequency generating) discs that are the transducers that vibrate to generate dry mist in the water while the ceramic discs are submerged below the water, while suspended on float 40*b*. In some embodiments, applicants have an ultrasonic oscillator with 12 discs mounted on a flat panel that is connected to a float so that the discs are suspended below the water surface and maintain at least a one-half inch below the water surface at all times to permit the generation of dry mist. The number of ultrasonic piezoelectric oscillator ceramic discs, to generate dry mist, which in one embodiment is 12, can vary widely, dependent on the water storage tank 30 and its function. In this embodiment, the invention 10 is a portable unit for sanitizing and/or disinfecting hard and soft surfaces and airborne particles with an ozone saturated dry mist. The ozone saturated dry mist ultrasonic oscillator 40 has an electrical connection that provides the proper voltage and amperage to each individual oscillator disc 40*a* that vibrates together and are all connected electrically parallel so the ceramic discs 40*a* all share the same voltage during operation. The ultrasonic oscillator 40, as a dry mist generator to create the dry mist to dissolve for the ozone to create an ozone saturated dry mist sanitizer and/or disinfectant, is also connected to the system electrical operating system that controls its power, on and off, and its operation at all times.

Figure 4:
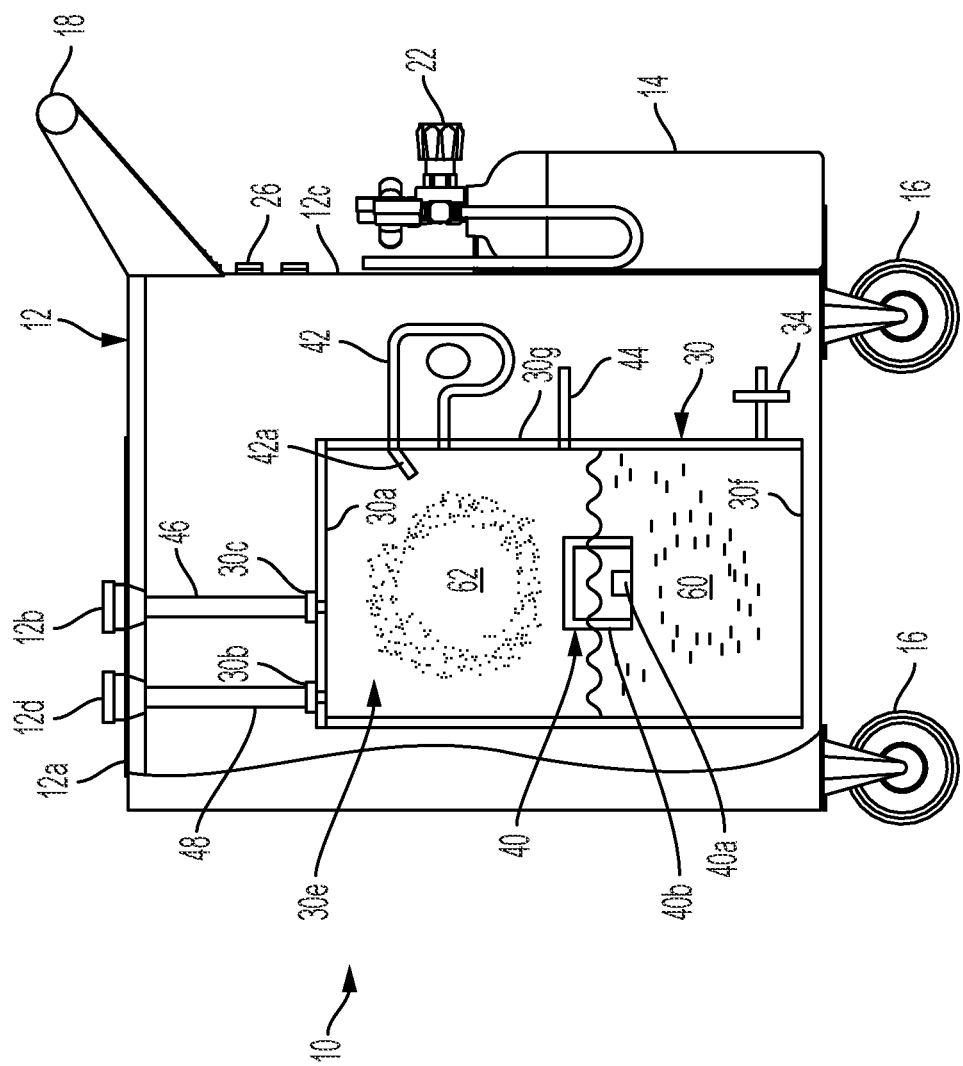

Referring to FIG. 1A and FIG. 4, the method or process of sanitizing, treating, sterilizing and/or disinfecting and/or deactivating hard and soft surfaces and airborne particles in the ambient air to eliminate bacteria and viruses, primarily focuses on creating an ozone saturated dry mist in the water storage tank 30 using the ultrasonic oscillator 40. An air blower 42 directs air, under low pressure, into the water storage tank 30 and downwardly toward the surface of the water therein, above the level of the ozone entering the water storage tank. Ozone generator 44 generates the ozone that is directed into the water storage tank above the surface of the water, below the incoming air flow from the air blower, to mix with the dry mist being generated by ultrasonic oscillator 40 dry mist generator. The purpose of the invention is to generate a desired ratio of dry mist in union with the ozone, to create an ozone saturated dry mist, so that when the sanitizer dispenser dispenses the ozone saturated dry mist under low pressure on a hard or soft surface and airborne particles, the proper ratio is provided for the zone to act to eliminate bacteria and viruses on a hard or soft surface and airborne particles and at the same time the ozone saturated dry mist evaporates from the surface quickly, so that a sanitized and/or disinfected surface does not get wet or damp or leave any deleterious residue. Applicants have determined that 80 to 90, and up to 150 parts per million of ozone in the dry mist is very effective as a sanitizer and/or disinfectant for bacteria and viruses on hard and soft surfaces without wetting the surfaces, not leaving a deleterious residue harmful to humans.

Referring now to FIG. 4, the invention system 10 is shown, with a side elevational view of exterior housing 12 cutaway on one side, so that the inside of the water storage tank 30 (viewed in cross-section) is represented schematically in operation, partially filled with water 60. The water storage tank 30 lower volume 30*f*, contains water 60. Above the water surface in the upper volume blending chamber 30*e* of water storage tank 30 is an ozone saturated dry mist 62 that has been generated by the ultrasonic oscillator 40 attached to float 40*b* on the surface of water 60. Ultrasonic oscillator discs 40*a* (FIG. 3) act as transducer frequency generators to generate dry mist 62 in the water storage tank 30, housed in the ultrasonic oscillator 40, and submerged to remain suspended below the water 60 surface. Also shown is the air blower 42 attached to the side wall of water storage tank 30 so that the air directed into the water storage tank upper area (above the water surface) containing the dry mist is directed downwardly by a diverter 42*a*, forcing the incoming air toward the water surface. Also mounted through the side wall of water storage tank 30 is the ozone generator 44 that also is positioned below the air blower 42 so that incoming ozone from ozone generator 44 is near the surface of the water 60 so that ozone interacts directly with the dry mist coming from the water surface and the downward air directed from air blower 42, creating ozone saturated dry mist 62 in the upper volume of water storage tank 30.

FIG. 4 shows conduits 46 and 48 each attached between the exterior housing panel 12*a* and the access fitting ports 12*b* and 12*d* and the water storage tank 30 access fitting ports 30*b* and 30*c*. Conduit 48 is used to supply water internally from the exterior housing 12 through access fitting port 12*d* into water storage tank access port 30*b*, for filling the water storage tank 30 when necessary. Conduit 46 is used to disperse the dry mist and ozone mixture sanitizer in blending chamber 30*e* to create an ozone saturated dry mist from water storage tank 30 through water storage tank access fitting 30*c* and exterior housing access fitting 12*b* connected to dispersing hose 52. (FIG. 1A). A nozzle 50 (FIG. 1A) may be attached on the end of the hose 52. The hose 52 and nozzle 50 direct the ozone saturated dry mist on hard and soft surfaces and airborne particles to be sanitized and/or disinfected. Therefore the system 10 is operated by providing power to air blower 42, ozone generator 44, and the ultrasonic oscillator 40 which has discs suspended underwater, approximately half an inch, that are vibrated to create the dry mist in the blending chamber 30*e* in the upper portion of water storage tank to create an ozone saturated dry mist 62. Also shown in FIG. 4 is a drain valve 34 which is connected outside of the exterior housing for emptying the water storage tank 30 of water.

The treating, dispensing, sanitizing, sterilizing, deactivating and/or disinfecting method and system can create a treating, sanitizing, sterilizing and/or disinfecting ozone saturated dry mist to sanitize and/or disinfect surfaces and airborne particles by creating a dispersed sanitizing evaporating dry mist vapor, super-saturated with ozone. The sanitizing ozone saturated dry mist is created using a pressure differential dispersant method. The ozone saturated dry mist will sanitize and or disinfect hard surfaces and airborne particles and penetrate porous surfaces and ambient air to sanitize and/or disinfect. It kills bacteria and viruses, and other pathogens on hard and soft surfaces and in ambient air.

In some embodiments, sanitizing apparatus utilizing the components, described in FIG. 1B—FIG. 3, can be mounted on a mobile platform, that includes wheels and a frame network with a handle, for manually moving and positioning an entire sanitation apparatus in various locations, which allow the delivery system to be positioned manually, thereby allowing a technician to thoroughly sanitize and/or disinfect an area with a mobile platform and the ability to manually position the output of the delivery system for sanitizing various surfaces.

The system of the present invention is for treating surfaces and airborne particles comprising. The system includes an exterior housing and an enclosed water storage tank mounted inside the exterior housing to store water. The system may also include a dry mist generator mounted on a water float to position the dry mist generator below a surface of the water stored in the enclosed water storage tank. The system may further include an air blower having an outlet connected to water storage tank above a predetermined water level. The system may still further include an oxygen tank having an outlet, and an ozone generator connected to the outlet of the oxygen tank. The system may also include a regulator and flow meter connected to the outlet of the oxygen tank and having an inlet conduit to the ozone generator to regulate a flow of oxygen into the ozone generator.

A volume of the water storage tank above the predetermined water level is defined as a blending chamber. Air dispensed from the air blower may be mixed with (or blended with) ozone dispensed from the ozone generator output to provide a mixture of ozone saturated dry mist having a predetermined saturation ratio of dry mist vapor and ozone. The system may further include an ozone saturated dry mist dispensing outlet for dispensing the ozone saturated dry mist.

The system according to the present invention may also be a mobile platform attached to the exterior housing. The air blower outlet may include an airflow diverter for diverting the output airflow in a direction of a surface of the water contained in the water storage tank. The dry mist may be generated at a rate of between about ⅕ liter per hour to 1 liter per hour, but those skilled in the art will appreciate that manipulation of any of the elements of the invention may provide generation of dry mist at any rate, and the flow rate listed above is not meant to limit the scope of the invention in any way.

The ozone generator may produce ozone at a rate of between about 3 grams per hour and 10 grams per hour. Those skilled in the art will appreciate that an ozone generator produces ozone at a rate outside of the above-referenced range may also be provided and is contemplated to be included within the scope of the present invention.

The air blower may generate air flow at a rate between about 5 cubic feet per minute and 15 cubic feet per minute. Those skilled in the art will appreciate that air flow may be generated from the air blower at any other volumetric rates and still be considered within the scope of the present invention.

The dry mist generator may be provided by an ultrasonic piezoelectric oscillator that includes one or more ceramic discs positioned to be submerged below the stored water surface. The one or more ceramic discs cause frequency vibration of the water to generate the dry mist in the water storage tank.

There are numerous examples of devices and articles that can be sanitized and disinfected of bacteria and viruses and other biological pathogens using the invention described herein, such as: modes of transportation, delivery vehicles, automobiles, trucks, ambulances, complete airplane including ventilation, trains, buses, spacecraft, subways, cruise ships, and boats; also buildings, including nursing homes, hotels, restaurants, motels, hospitals, office spaces, grocery stores, grocery carts; food processing, buffets and salad bars, kitchens and food preparation service areas; and indoor and outdoor furniture.

The foregoing is considered as illustrative only of the principles of the invention. Numerous changes and modifications will readily occur to those skilled in the art, as it is not desired to limit the invention to the exact construction and operation shown and described, and accordingly, all such suitable changes or modifications in structure and operation which may be resorted to are intended to fall within the scope of the claimed invention.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

The invention claimed is:

1. A system for treating, sanitizing, sterilizing, and/or disinfecting surfaces and airborne particles containing bacteria and/or viruses comprising:
   an exterior housing;
   an enclosed water storage tank mounted inside the exterior housing, the enclosed water storage tank configured to store a water supply for creating ozone saturated dry misty above a stored water surface level of the water supply stored in the enclosed water storage tank;
   an ultrasonic piezoelectric oscillator having ceramic disks and; mounted on a water float so as to position the ceramic disks of the ultrasonic piezoelectric oscillator at least half of an inch below the stored water surface level to generate dry mist;

an air blower for generating air under pressure and positioned outside of the enclosed water storage tank, the air blower having an outlet connected to an air blower outlet of a side wall of the enclosed water storage tank above a predetermined water level permitted in the enclosed water storage tank;

an airflow diverter positioned downwardly on an upper portion of the air blower outlet and within the enclosed water storage tank for diverting air dispensed from the air blower downwardly towards the stored water surface level within the enclosed water storage tank;

an oxygen tank having an outlet to provide oxygen;

an ozone generator connected to the outlet of the oxygen tank to receive oxygen therefrom and to generate and output ozone with the oxygen received;

a regulator and flow meter connected to the outlet of the oxygen tank and having an inlet conduit to the ozone generator for regulating the flow of oxygen into the ozone generator from the oxygen tank;

a blending chamber defined by a volume within the enclosed water storage tank above the stored water surface level to mix the air dispensed from the air blower, the ozone generated by the ozone generator, and the dry mist generated by the ultrasonic piezoelectric oscillator to provide a mixture of ozone saturated dry mist having a predetermined saturation ratio of dry mist vapor and ozone in parts per million of ozone; and a plurality of ozone saturated dry mist dispensing outlets that are each connected to a respective one of a plurality of access fitting ports positioned on a top surface of the enclosed water storage tank; and wherein each of the plurality of ozone saturated dry mist dispensing outlets provide access to pour water into the enclosed water storage tank and the plurality of ozone saturated dry mist dispensing outlets are connectable to a dispensing hose for dispensing the mixture of ozone saturated dry mist provided by the blending chamber.

2. The system according to claim 1 further comprising a mobile platform attached to the exterior housing for treating surfaces and airborne particles.

3. The system according to claim 1 wherein the dry mist is generated at a rate of between about ⅕ liter per hour to 1 liter per hour.

4. The system according to claim 1 wherein the ozone generator outputs ozone at a rate of between about 3 grams per hour and 10 grams per hour; and wherein the air blower generates air flow at a rate between about 5 cubic feet per minute and 15 cubic feet per minute.

5. The system according to claim 1 wherein the ceramic discs of the ultrasonic piezoelectric oscillator cause frequency vibration of the water to generate the dry mist in the enclosed water storage tank.

6. A system for treating surfaces and airborne particles comprising:

an exterior housing;

an enclosed water storage tank mounted inside the exterior housing to store water;

a dry mist generator having ceramic disks and mounted on a water float to position the ceramic disks of the dry mist generator at least half of an inch below a surface of the water stored within the enclosed water storage tank;

an air blower for generating air under pressure and positioned outside of the enclosed water storage tank, the air blower having an outlet connected to an air blower outlet of a side wall of the enclosed water storage tank above a predetermined water surface level;

an oxygen tank having an outlet to provide oxygen;

an ozone generator connected to the outlet of the oxygen tank and receive oxygen therefrom to generate and output ozone with the oxygen received;

a regulator and flow meter connected to the outlet of the oxygen tank and having an inlet conduit to the ozone generator to regulate a flow of oxygen into the ozone generator from the oxygen tank; and a blending chamber defined by a volume within the enclosed water storage above the predetermined water surface level, wherein the air dispensed from the air blower is mixed with the ozone generated by the ozone generator and with the dry mist generated by the dry mist generator within the blending chamber to provide a mixture of ozone saturated dry mist having a predetermined saturation ratio of dry mist vapor and ozone; and a plurality of ozone saturated dry mist dispensing outlets that are each connected to a respective one of a plurality of access fitting ports positioned on a top surface of the enclosed water storage tank.

7. The system according to claim 6, further comprising a mobile platform attached to the exterior housing.

8. The system according to claim 6 wherein the dry mist is generated at a rate of between about ⅕ liter per hour to 1 liter per hour.

9. The system according to claim 6 wherein the ozone generator produces ozone at a rate of between about 3 grams per hour and 10 grams per hour.

10. The system according to claim 6 wherein the air blower generates air flow at a rate between about 5 cubic feet per minute and 15 cubic feet per minute.

11. The system according to claim 6 wherein the ceramic discs of the dry mist generator cause frequency vibration of the water to generate the dry mist in the enclosed water storage tank.

12. The system according to claim 11 wherein the dry mist generator comprises an ultrasonic piezoelectric oscillator.

13. The system according to claim 6 further comprising at least one status light mounted on the exterior housing that provides at least one status of the system.

14. The system according to claim 6 further comprising at least one sensor carried by the enclosed water storage tank and configured to determine a water level of water stored in the enclosed water storage tank.

15. The system according to claim 6 further comprising an electrical control unit configured to control the air blower, the ozone generator, and the regulator and flow meter.

16. The system according to claim 6 wherein each of the plurality of ozone saturated dry mist dispensing outlets provide access to pour water into the enclosed water storage tank, and wherein the plurality of ozone saturated dry mist dispending outlets are connectable to a dispensing hose for dispensing the mixture of ozone saturated dry mist provided by the blending chamber.

17. The system according to claim 6 further comprising an airflow diverter positioned downwardly on an upper portion of the air blower outlet and within the water storage tank for diverting air dispensed from the air blower downwardly towards the surface of the water stored within the enclosed water storage tank.

* * * * *